US00PP13633P29

(12) United States Plant Patent
Trees

(10) Patent No.: US PP13,633 P2
(45) Date of Patent: Mar. 11, 2003

(54) GERANIUM PLANT NAMED 'BALGALBRIO'

(75) Inventor: Scott C. Trees, Shell Beach, CA (US)

(73) Assignee: Ball FloraPlant, a division of Ball Horticultural Co., West Chicago, IL (US)

( * ) Notice: Subject to any disclaimer, the term of this patent is extended or adjusted under 35 U.S.C. 154(b) by 0 days.

(21) Appl. No.: 10/115,057

(22) Filed: Apr. 1, 2002

(51) Int. Cl.[7] ..... A01H 5/00

(52) U.S. Cl. ..... Plt./324

(58) Field of Search ..... Plt./324, 328, 332, Plt./329

*Primary Examiner*—Kent Bell
(74) *Attorney, Agent, or Firm*—C. A. Whealy

(57) ABSTRACT

A new and distinct cultivar of Geranium plant named 'Balgalbrio', characterized by its outwardly spreading and mounded growth habit; freely basal branching habit; dark green-colored leaves with a distinct zonation pattern; and red purple-colored semi-double flowers.

1 Drawing Sheet

BOTANICAL CLASSIFICATION/CULTIVAR DESIGNATION

*Pelargonium×hortorum×Pelargonium peltatum* cultivar 'Balgalbrio'.

BACKGROUND OF THE INVENTION

The present invention relates to a new and distinct cultivar of Geranium plant, botanically known as *Pelargonium×hortorum×Pelargonium peltatum*, and hereinafter referred to by the name 'Balgalbrio'.

The new Geranium is a product of a planned breeding program conducted by the Inventor in Arroyo Grande, Calif. The objective of the breeding program is to develop new interspecific Geranium cultivars with outwardly spreading growth habit, uniform flowering, and interesting flower and foliage colors.

The new Geranium originated from a cross-pollination made by the Inventor in June, 2000 of a proprietary *Pelargonium×hortorum* selection identified as code number 867-21, not patented, as the female, or seed, parent with a proprietary *Pelargonium peltatum* selection identified as code number 1018-3, not patented, as the male, or pollen, parent. The cultivar 'Balgalbrio' was discovered and selected by the Inventor as a flowering plant within the progeny from this cross-pollination in a controlled environment in Arroyo Grande, Calif.

Asexual reproduction of the new cultivar by terminal cuttings taken at Arroyo Grande, Calif., since June, 2000 has shown that the unique features of this new Geranium are stable and reproduced true to type in successive generations of asexual reproduction.

SUMMARY OF THE INVENTION

The following traits have been repeatedly observed and are determined to be the unique characteristics of 'Balgalbrio'. These characteristics in combination distinguish 'Balgalbrio' as a new and distinct Geranium cultivar:

1. Outwardly spreading and mounded growth habit.
2. Freely basal branching habit.
3. Dark green-colored leaves with a distinct zonation pattern.

4. Red purple-colored semi-double flowers.

Plants of the new Geranium differ primarily from plants of the female parent selection in flower coloration. Plants of the new Geranium differ primarily from plants of the male parent selection in leaf and flower coloration.

The new Geranium can be compared to the cultivar, 'Balgalpipn', disclosed in U.S. Plant Pat. No. 11,925. However, in side-by-side comparisons conducted in West Chicago, Ill., plants of the new Geranium differed from plants of the cultivar 'Balgalpipn' in the following characteristics:

1. Plants of the new Geranium had fewer leaves per lateral branch than plants of the cultivar 'Balgalpipn'.
2. Leaves of plants of the new Geranium had a distinct zonation pattern whereas leaves of plants of the cultivar 'Balgalpipn' did not have a distinct zonation pattern.
3. Plants of the new Geranium had fewer petals per flower than plants of the cultivar 'Balgalpipn'.
4. Plants of the new Geranium had longer peduncles than plants of the cultivar 'Balgalpipn'.

BRIEF DESCRIPTION OF THE PHOTOGRAPH

The accompanying colored photograph illustrates the overall appearance of the new cultivar, showing the colors as true as it is reasonably possible to obtain in colored reproductions of this type.

The photograph comprises a side perspective view of a typical flowering plant of 'Balgalbrio'. Flower and foliage colors in the photograph differ slightly from the color values cited in the detailed botanical description which accurately describe the colors of the new Geranium.

DETAILED BOTANICAL DESCRIPTION

The cultivar 'Balgalbrio' has not been observed under all possible environmental conditions. The phenotype may vary somewhat with variations in environment such as temperature and light intensity, without, however, any variance in genotype. The aforementioned photograph and following observations and measurements describe plants grown in West Chicago, Ill., under commercial practice in a polycarbonate-covered greenhouse with day temperatures about 18 to 26° C., night temperatures about 18 to 26° C. and light levels about 3,500 to 5,000 foot-candles. Plants used for the photograph and description were about eight to ten weeks from planting rooted cuttings. In the following description, color references are made to The Royal Horticultural Society Colour Chart, 1995 Edition, except where general terms of ordinary dictionary significance are used.

Botanical classification: *Pelargonium×hortorum×Pelargonium peltatum* cultivar 'Balgalbrio'.

Parentage:

*Female parent.*—Proprietary *Pelargonium×hortorum* selection identified as code number 867-21, not patented.

*Male parent.*—Proprietary *Pelargonium peltatum* selection identified as code number 1018-3, not patented.

Propagation:

*Type cutting.*—Terminal cuttings.

*Time to initiate roots.*—About 7 days at 18° C.

*Time to develop roots.*—About 21 days at 18° C.

*Root description.*—Fibrous, freely branching.

Plant description:

*General appearance.*—Outwardly spreading and mounded growth habit. Appropriate for 10-cm and larger containers.

*Growth and branching habit.*—Vigorous and freely basal branching with about three lateral branches at the base. Pinching, that is, removal of terminal apices, is typically not required.

*Plant height* (*to top of foliage*).—About 18.8 cm.

*Plant width.*—About 25.9 cm.

*Lateral branches.*—Length: About 16.1 cm. Internode length: About 1.9 cm. Texture: Pubescent. Color: 143B.

*Foliage description.*—Arrangement: Opposite, simple. Quantity of leaves per lateral branch: About six. Length: About 5.7 cm. Width: About 9.2 cm. Shape: Reniform. Apex: Rounded. Base: Cordate. Margin: Crenate. Venation: Palmate. Texture, upper and lower surfaces: Velvety; pubescent. Color: Young and fully expanded foliage, upper surface: 137A; zonation pattern, 187A in color and located at the center of the leaf. Young and fully expanded foliage, lower surface: 137C. Venation, upper surface: 144B. Venation, lower surface: 143C. Petiole: Length: About 8.6 cm. Diameter: About 2.6 mm. Texture, upper and lower surfaces: Pubescent. Color, upper and lower surfaces: 143C.

Flower description:

*Flower arrangement and type.*—Single flowers arranged in hemispherical umbels arising from apical leaf axils. Umbels displayed above the foliage. At full flowering, usually about six open umbels and about four developing umbels per plant. Flowers semi-double and rounded in shape. Umbels persistent. Flowers not fragrant.

*Flowering season.*—Year-round under greenhouse conditions. In the garden, flowering is continuous from spring until fall. Plants start flowering about eight weeks after planting.

*Flower longevity.*—Flowers last about ten days on the plant.

*Umbels.*—Diameter: About 8.1 cm. Height: About 5.2 cm. Number of flowers per umbel: About ten. Flower diameter: About 4.3 cm. Flower depth (height): About 1.7 cm.

*Flower buds.*—Length: About 1.4 cm. Diameter: About 7 mm. Shape: Ovoid. Color: 71A.

*Petals/petaloids.*—Quantity: About six petals and about five petaloids per flower. Petaloids variable in size and shape. Arrangement: Imbricate. Petal length: Upper petals: About 2.5 cm. Lower petals: About 2.3 cm. Petal width: Upper petals: About 1.9 cm. Lower petals: About 1.9 cm. Petal shape: Obovate. Petal/petaloid apex: Rounded, obtuse. Petal/petaloid base: Attenuate. Petal/petaloid margin: Entire. Petal/petaloid texture, upper and lower surfaces: Smooth. Petal/petaloid aspect: Slightly cupped. Petal/petaloid color: When opening and fully opened, upper petals, upper surface: 74B; spot, 61C, towards base; base, 155D; main color becoming closer to 80B with subsequent development; venation, 71C. When opening and fully opened, lower petals, upper surface: 74B; venation, 64B. When opening and fully opened, upper and lower petals, lower surface: 73A; venation, 64B.

*Sepals.*—Quantity: Five per flower; not imbricate on open flowers. Length: About 1.9 cm. Width: About 3 mm. Shape: Ensiform to lanceolate. Apex: Acuminate. Margin: Entire. Texture, upper surface: Glabrous. Texture, lower surface: Pilose. Color, upper and lower surfaces: 143A.

*Peduncle* (*umbel stem*).—Length: About 18.5 cm. Angle: Erect. Strength: Strong. Texture: Pubescent. Color: 143A.

*Pedicel* (*individual flower stem*).—Length: About 3.2 cm. Angle: Erect. Strength: Strong. Texture: Pubescent. Color: 143A overlain with 187A.

*Reproductive organs.*—Androecium: Anther quantity: Five per flower. Anther length: About 3 mm. Anther color: 71A. Pollen amount: Moderate. Pollen color: 167A. Gynoecium: Pistil quantity: One per flower. Pistil length: About 1.1 cm. Stigma shape: Five or six-parted, star-shaped. Stigma color: 64A. Style length: About 2 mm. Style color: 64A.

*Seed/fruit.*—None observed.

Disease/pest resistance: Resistance to pathogens and pests common to Pelargonium has not been observed.

It is claimed:

1. A new and distinct cultivar of Geranium plant named 'Balgalbrio', as herein illustrated and described.

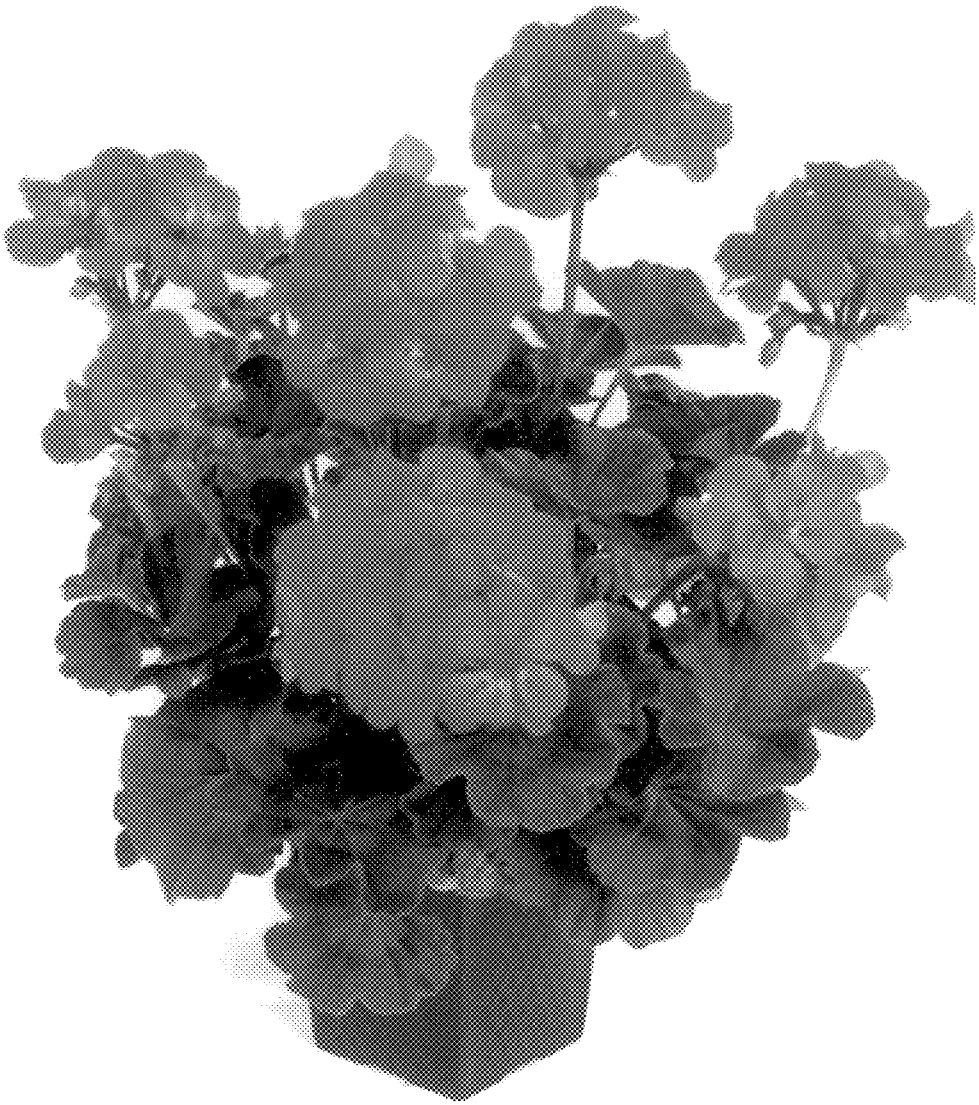

* * * * *